United States Patent
Wolf et al.

(10) Patent No.: US 9,465,016 B2
(45) Date of Patent: Oct. 11, 2016

(54) CHROMATOGRAPHIC SYSTEM AND METHOD OF ISOLATING COMPOUND IN SAMPLE USING CHROMATOGRAPHIC SYSTEM

(71) Applicant: AGILENT TECHNOLOGIES, INC., Loveland, CO (US)

(72) Inventors: Frank Wolf, Karlsruhe (DE); Vlastimil Hruska, Waldbronn (DE); Andreas Tei, Mannheim (DE); Manuel Renz, Sinzheim (DE)

(73) Assignee: Agilent Technologies, Inc., Santa Clara, CA (US)

( * ) Notice: Subject to any disclaimer, the term of this patent is extended or adjusted under 35 U.S.C. 154(b) by 334 days.

(21) Appl. No.: 14/154,689

(22) Filed: Jan. 14, 2014

(65) Prior Publication Data
US 2015/0198572 A1 Jul. 16, 2015

(51) Int. Cl.
*G01N 30/80* (2006.01)
*G01N 30/86* (2006.01)
G01N 30/02 (2006.01)
B01D 15/16 (2006.01)
G01N 30/34 (2006.01)

(52) U.S. Cl.
CPC ......... *G01N 30/8658* (2013.01); *B01D 15/166* (2013.01); *G01N 30/34* (2013.01); *G01N 2030/027* (2013.01)

(58) Field of Classification Search
None
See application file for complete search history.

(56) References Cited

U.S. PATENT DOCUMENTS

| | | | |
|---|---|---|---|
| 5,987,959 A * | 11/1999 | Klee | G01N 30/32 73/1.02 |
| 2012/0096919 A1* | 4/2012 | Choikhet | G01N 30/24 73/1.02 |

OTHER PUBLICATIONS

Dolan, J. and Snyder, L. 2012. Gradient Elution Chromatography. Encyclopedia of Analytical Chemistry. DOI: 10.1002/9780470027318.a5907.pub2.*
Schoenmakers et al., "Gradient Selection in Reversed-Phase Liquid Chromatography", Journal of Chromatography 149, (1978) pp. 519-537.

(Continued)

*Primary Examiner* — Hezron E Williams
*Assistant Examiner* — Mark A Shabman (57) ABSTRACT

A method is provided for isolating a compound in a sample by chromatography. The method includes determining an analytical gradient of an analytical system; performing an analytical run using the analytical gradient; identifying a target compound in the sample and determining an analytical retention time of the target compound using chromatographic results of the analytical run; determining an elution point of the target compound using the analytical retention time, the analytical gradient and characteristics of the analytical system; determining automatically a focusing gradient of a preparative system, including a slope segment; and performing a preparative run using the focusing gradient to separate the target compound from the sample. The slope segment includes a slope determining a concentration of solvent in a solvent mixture, which linearly increases from a first offset below the elution point of the target compound to a second offset above the elution point of the target compound.

19 Claims, 5 Drawing Sheets

(56) References Cited

OTHER PUBLICATIONS

Davy Guillarme et al., "Method transfer for fast liquid chromatography in pharmaceutical analysis: Application to short columns packed with small particle. Part II: Gradient experiments", European Journal of Pharmaceutics and Biopharmaceutics, 68 (2008), pp. 430-440.

Schoenmakers et al., "Gradient Selection in Reversed-Phase Liquid Chromatography", Journal of Chromatography 149, (1978) pp. 519-536.

* cited by examiner

CHROMATOGRAPHIC SYSTEM AND METHOD OF ISOLATING COMPOUND IN SAMPLE USING CHROMATOGRAPHIC SYSTEM

BACKGROUND

In conventional chromatographic purification workflows, it is common to perform a scouting process on a sample in a solvent mixture using an analytical system (referred to as an analytical run) before performing a purification process for isolating a target compound contained in the sample using a preparative system (referred to as a preparative run). The purpose of the analytical run is to identify the target compound and to select a suited predefined focusing gradient. For this purpose, the chromatogram from the analytical run is subdivided into several time windows.

A chemist then writes a focusing gradient for each time window for subsequent preparative runs, generally based on the chemist's experience. In a manual workflow, the user will determine, also generally based on experience, in which time window the peak of interest (of the target compound) elutes, and will assign the appropriate focusing gradient to this time window. The determination of the time window of the target compound and assignment of a predefined focusing gradient may be automated. However, using this approach, when a parameter of the chromatographic system, such as flow, column length, column inner-diameter (ID), or analytical runtime, has been changed, all predefined focusing gradients need to be adapted or completely rewritten. This process again requires involvement of an experienced chemist. Further, the number of applied time windows is usually small (e.g., three to ten time windows), which leads to a very rough classification of analytical retention times, often resulting in inappropriate selection of preparative gradients.

Accordingly, there is a need for an automated chromatographic system that does not rely upon predefined preparative focusing gradients, determined by an experienced chemist in advance, or otherwise require preparative focusing gradients to be redefined after one or more chromatographic system parameters have changed.

SUMMARY

In a representative embodiment, a method is provided for isolating a compound in a sample, including multiple compounds, by chromatography. This includes determining an analytical gradient of an analytical system; performing an analytical run using the analytical gradient; identifying a target compound in the sample using chromatographic results of the analytical run; determining an analytical retention time of the target compound using the chromatographic results of the analytical run; determining an elution point of the target compound using the analytical retention time, the analytical gradient and characteristics of the analytical system; determining automatically a focusing gradient of a preparative system, up-scaled from the analytical gradient, the focusing gradient including a slope segment; and performing a preparative run using the focusing gradient to separate the target compound from the sample. The slope segment of the focusing gradient includes a slope determining a concentration of solvent in a solvent mixture, the concentration linearly increasing from a first offset below the elution point of the target compound to a second offset above the elution point of the target compound.

In another representative embodiment, a method is provided for isolating a target compound in a sample using an automatically determined focusing gradient in a preparative system. The method includes determining an analytical dwell volume of an analytical system, and a preparative dwell volume of the preparative system; determining an analytical column void volume of an analytical column in the analytical system, and a preparative column void volume of a preparative column in the preparative system; determining an analytical gradient of the analytical system; determining a point of elution of the target compound based on at least the analytical dwell volume, the analytical column void volume and an analytical retention time of the target compound obtained using chromatographic results of an analytical run on solvent mixture having a concentration of organic solvent that linearly increases in accordance with a slope of the analytical gradient; and determining automatically a focusing gradient of the preparative system based on at least the analytical and preparative dwell volumes, the analytical and preparative column void volumes, analytical and preparative pump flows of the solvent mixture, and the determined point of elution of the target compound. Determining automatically the focusing gradient includes determining a slope, providing the concentration of the organic solvent in the solvent mixture that linearly increases from a first offset below the point of elution of the target compound at a beginning of a slope segment of the focusing gradient to a second offset above the point of elution of the target compound at an end of the slope segment of the focusing gradient.

In another representative embodiment, a chromatographic system includes an analytical system and a preparative system. The analytical system is configured to perform an analytical chromatographic run by applying an analytical gradient, to identify a target compound in a sample and a corresponding retention time using chromatographic results of the analytical run, and to determine an elution point of the target compound based on the analytical retention time of the target compound, the analytical gradient and characteristics of the analytical system including an analytical dwell volume and dimensions of an analytical column. The preparative system is configured to develop automatically a focusing gradient based on the elution point of the target compound and characteristics of the preparative system including a preparative dwell volume and dimensions of a preparative column, and to perform a preparative chromatographic run by applying the focusing gradient to separate the target compound from the sample. The dimensions of the preparative column are larger than the dimensions of the analytical column. Also, the automatically developed focusing gradient comprises a slope segment having a slope determining concentration of an organic solvent in a solvent mixture carrying the sample, the concentration linearly increasing from a first offset below the elution point of the target compound to a second offset above the elution point of the target compound, the first and second offsets being adjustable so that the target compound elutes within the slope segment.

BRIEF DESCRIPTION OF THE DRAWINGS

The representative embodiments are best understood from the following detailed description when read with the accompanying drawing figures. Wherever applicable and practical, like reference numerals refer to like elements.

DETAILED DESCRIPTION

In the following detailed description, for purposes of explanation and not limitation, illustrative embodiments disclosing specific details are set forth in order to provide a thorough understanding of embodiments according to the present teachings. However, it will be apparent to one having had the benefit of the present disclosure that other embodiments according to the present teachings that depart from the specific details disclosed herein remain within the scope of the appended claims. Moreover, descriptions of well-known devices and methods may be omitted so as not to obscure the description of the example embodiments. Such methods and devices are within the scope of the present teachings.

Generally, it is understood that as used in the specification and appended claims, the terms "a", "an" and "the" include both singular and plural referents, unless the context clearly dictates otherwise. Thus, for example, "a device" includes one device and plural devices.

As used in the specification and appended claims, and in addition to their ordinary meanings, the terms "substantial" or "substantially" mean to within acceptable limits or degree. For example, "substantially cancelled" means that one skilled in the art would consider the cancellation to be acceptable. As a further example, "substantially removed" means that one skilled in the art would consider the removal to be acceptable.

As used in the specification and the appended claims and in addition to its ordinary meaning, the term "approximately" means to within an acceptable limit or amount to one having ordinary skill in the art. For example, "approximately the same" means that one of ordinary skill in the art would consider the items being compared to be the same.

Generally, the various embodiments are directed to automatic development of a focusing gradient in a preparative run by a preparative system for a target compound with respect to the point of elution of the target compound. The point of elution is calculated, e.g., by software executed by a processor, on the percentage of organic solvent applied during an analytical (or ballistic) gradient in an analytical run by an analytical system. Preparative compound focusing gradients are automatically developed (as opposed to pre-determined or individually determined by a chemist) based on the target compound's analytical point of elution, the analytical gradient, dwell volumes of the analytical and preparative systems, and analytical and preparative column dimensions. Each of the developed focusing gradients contains multiple segments, including a preparative column equilibration segment, an isocratic hold segment, a variable slope segment, and a flushing (or purging) segment. The slope segment is placed around the analytical point of elution of the target compound.

Figure 1:
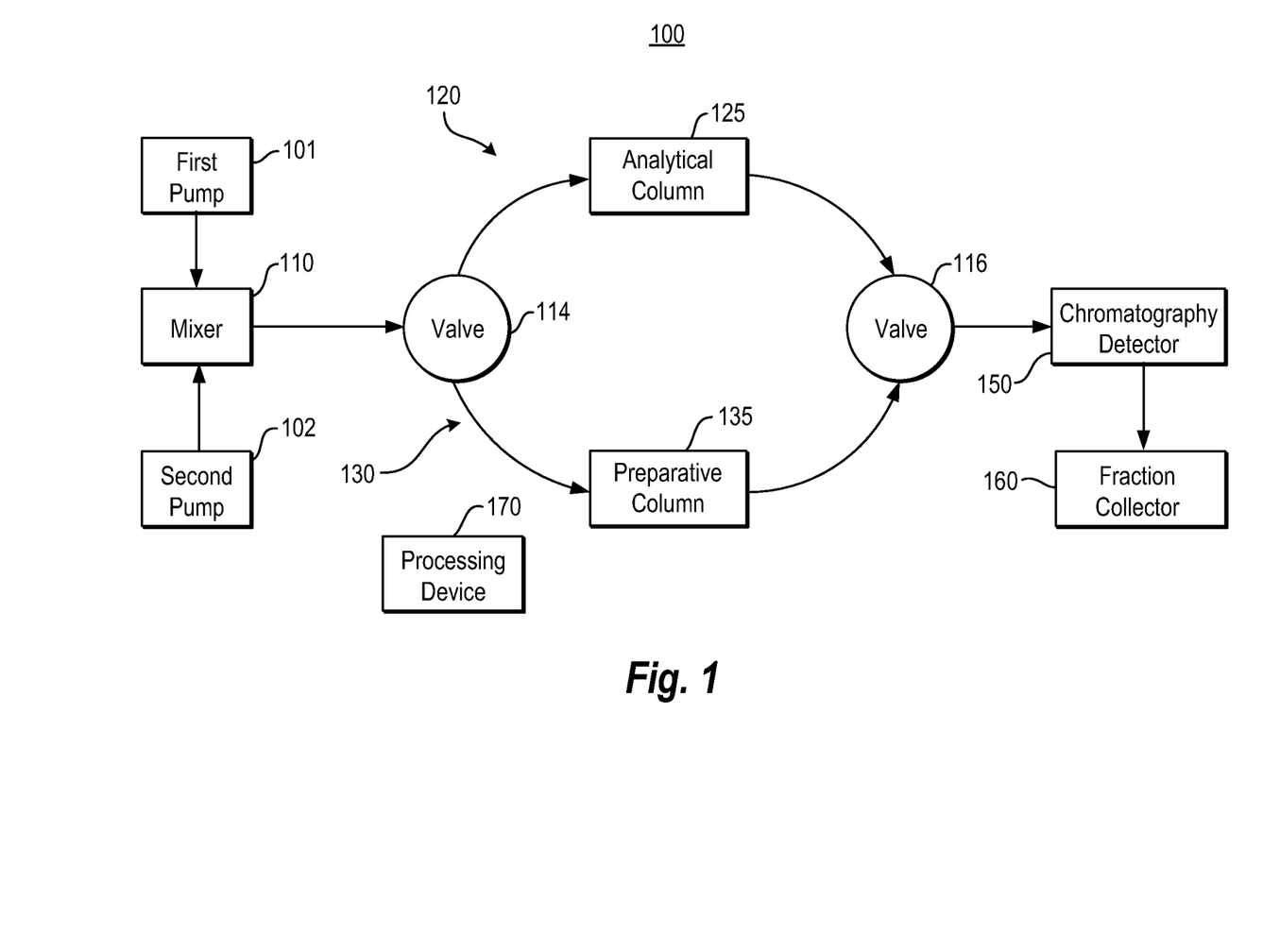
FIG. 1 is a simplified block diagram of a chromatographic system, including an analytical system and a preparative system, according to a representative embodiment.

FIG. 1 is a simplified block diagram of a chromatographic system, including an analytical system and a preparative system, according to a representative embodiment.

Referring to FIG. 1, chromatographic system 100 includes an analytical system 120, a preparative system 130 and a mixer 110, which is fed by first pump 101 and second pump 102, for providing a solvent mixture containing varying concentrations of organic solvent to one of the analytical system 120 and the preparative system 130. For example, the first pump 101 may provide a liquid carrier, such as water, from a first reservoir (not shown) and the second pump 102 may provide an organic solvent, such as acetonitrile, from a second reservoir (not shown). Of course, other liquid carriers and solvents (organic and inorganic) may be incorporated without departing from the scope of the present teachings. The mixer 110 is controlled to mix the liquid carrier received from the first pump 101 and the organic solvent received from the second pump 102 in a determined ratio to provide a solvent mixture having a desired concentration of organic solvent, which is the percentage of organic solvent making up the total solvent mixture. As described further below, the first pump 101, the second pump 102 and the mixer 110 are controlled so that the concentration of organic solvent varies anywhere from 0 to 100 percent, in accordance with a gradient of the analytical system 120 (i.e., the analytical gradient) or the preparative system 130 (i.e., the focusing gradient).

Each of the analytical system 120 and the preparative system 130 is connected between a first valve 114 and a second valve 116. The mixer 110 provides the solvent mixture to the first valve 114, which is controlled to direct the solvent mixture to one of the analytical system 120 for performing an analytical run or to the preparative system 130 for performing a preparative run. In each of the analytical and preparative runs, a sample containing one or more compounds is injected into the solvent mixture and the compounds elute in response to increasing concentrations of organic solvent (e.g., via the second pump 102). The analytical run may be performed at an analytical pump flow (e.g., about 1.5 ml/min) and the preparative run may be performed at preparative pump flow (e.g., about 30 ml/min).

Generally, according to various embodiments, the analytical system 120 is used to select or otherwise identify a target compound from among the compounds in sample, while the preparative system 130 may be used to isolate and/or collect the target compound, referred to as purifying the sample. The second valve 116 is controlled to direct the output of the analytical system 120 or the preparative system 130 to a chromatography detector 150, such as an ultraviolet (UV) detector, for example. The chromatography detector 150 is configured to detect and identify compounds being eluted off the analytical column 125 during an analytical run and being eluted off the preparative column 135 during a preparative run. The output of the chromatography detector 150 is provided to a fraction collector 160, which is configured to collect the target compound isolated from the other compounds in the sample during the preparative run.

The chromatographic system 100 also includes a processing device 170. The processing device 170 may be implemented by one or more computer processors, application specific integrated circuits (ASICs), field-programmable gate arrays (FPGAs), or combinations thereof, using software, firmware, hard-wired logic circuits, or combinations thereof, as discussed further below. The processing device 170 may be configured to control all or part of the operations of the chromatographic system 100 described herein for isolating a target compound in a sample using chromatography. For example, the processing device 170 may be configured to control the first pump 101, the second pump 102 and/or the mixer 110 to provide desired concentrations of organic solvent in the solvent mixture according to analytical and preparative gradients, and to control the first and second valves 114 and 116 to direct the solvent mixture through one of the analytical system 120 and the preparative system 130.

The analytical system 120 includes an analytical column 125, which provides the stationary phase causing the compounds in the sample to elute at different times, referred to as retention times, as the concentration of the organic solvent increases in accordance with an analytical gradient applied during the analytical run. The analytical column 125 has a column void volume determined by the inner diameter and the length of the analytical column 125, as well as the porosity (percentage of free space around the analytical column packing material/particles). The analytical system 120 overall has a dwell volume essentially determined by the remaining volume of the analytical system 120 through which the solvent mixture passes, from the mixer 110 to the head of the analytical column 125. For example, the analytical column 125 may be a standard size, having an inner diameter of about 4.6 mm, a length of about 150 mm and a porosity of about 53 percent for a column void volume of about 1.32 ml, and may include particles with a size of about 5 μm. Also, for example, the dwell volume of the analytical system 120 may be about 200 μl-1000 μl. Of course, the various volumes and other characteristics of the analytical system 120 may vary without departing from the scope of the present teachings. For example, the analytical gradient may be scaled to analytical columns having different lengths. As would be apparent to one of ordinary skill in the art. The scaling may be performed using known gradient up-scaling formulas, examples of which are described by Guillarme et al., *Method Transfer for Fast Liquid Chromatograph in Pharmaceutical Analysis: Application to Short Columns Packed with Small Particles. Part II: Gradient Experiments*, European Journal of Pharmaceutics and Biopharmaceutics, 68, pp. 430-440 (2008) (hereinafter "Guillarme et al."), the entire subject matter of which is hereby incorporated by reference.

Generally, the preparative system 130 is dimensionally larger than the analytical system 120. The preparative system 130 includes a preparative column 135, which provides the stationary phase causing the compounds in the sample to elute at different times as the concentration of the organic solvent increases in accordance with a focusing gradient applied during the preparative run. The preparative column 135 has a column void volume determined by its inner diameter, length and the porosity (percentage of free space around the column packing material/particles). Also, the preparative system 130 overall has a dwell volume essentially determined by the remaining volume of the preparative system 130 through which the solvent mixture passes, from the mixer 110 to the head of the preparative column 135. For example, the preparative column 135 may have an inner diameter of about 21.2 mm, a length of about 150 mm and a porosity of about 53 percent for a column void volume of about 28.07 ml, and may include particles with a size of about 5 μm. Also, for example, the dwell volume of the preparative system 130 may be about 6000 μl. Of course, the various volumes and other characteristics of the preparative system 130 may vary without departing from the scope of the present teachings. Scaling likewise may be performed using the known gradient up-scaling formulas mentioned above, for example, to determine the isocratic hold segment of the preparative focusing gradient (discussed below) and to scale duration of the slope segment of the focusing gradient if a column length of the preparative column 135 is greater than a column length of the analytical column 125 (e.g., about 150 mm).

Figure 2:
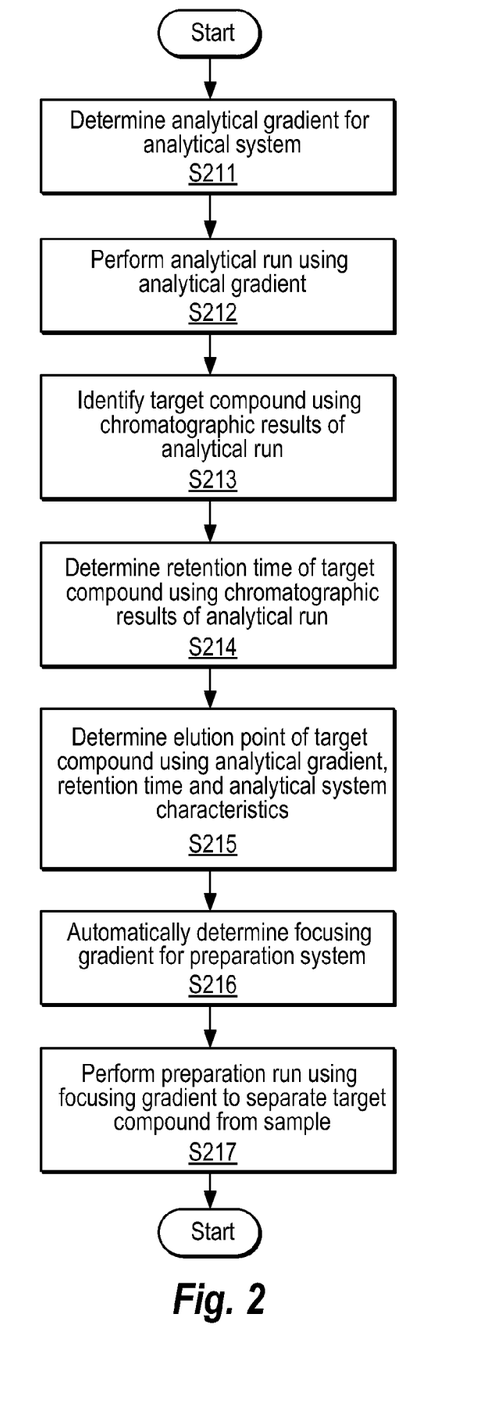
FIG. 2 is a flow diagram depicting a method of isolating a compound in a sample by chromatography, according to a representative embodiment.
Figure 3:
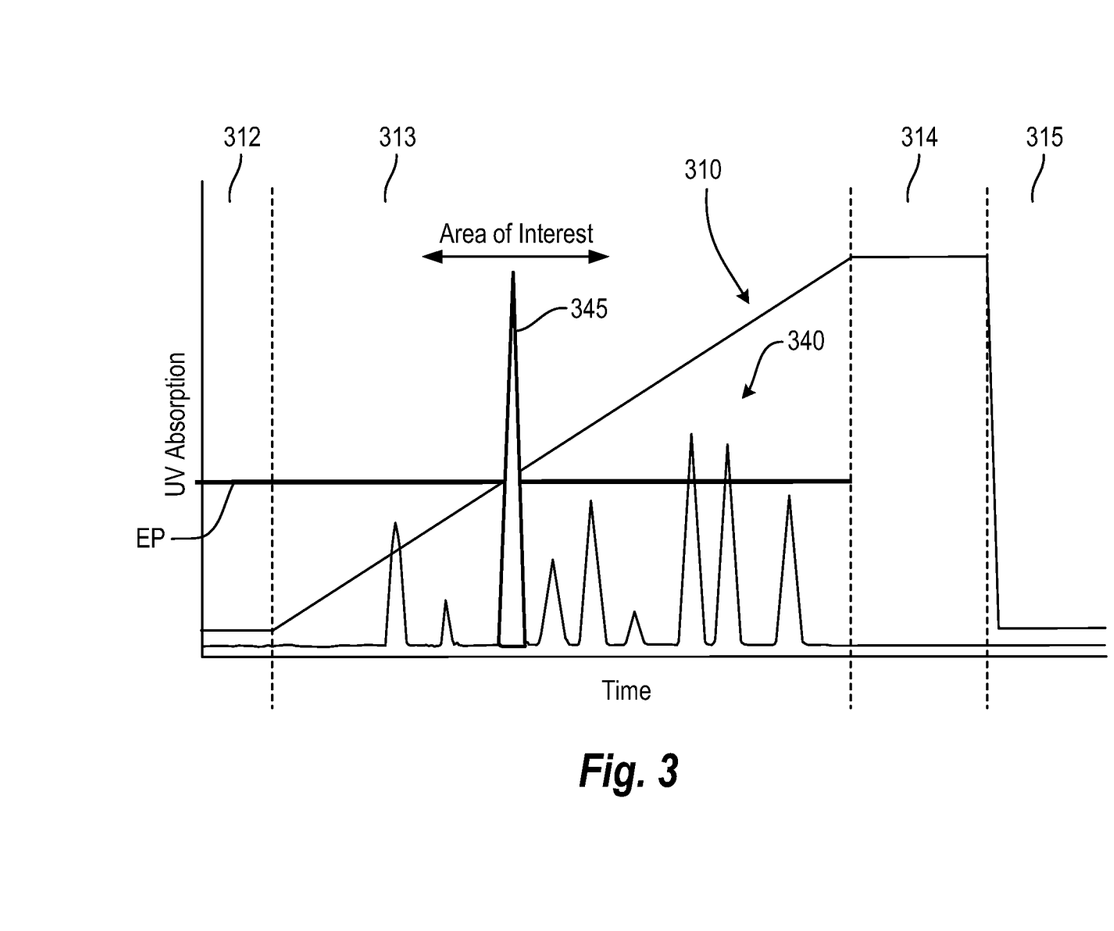
FIG. 3 is a diagram showing chromatographic results of an analytical run using an analytical gradient, according to a representative embodiment.
Figure 4:
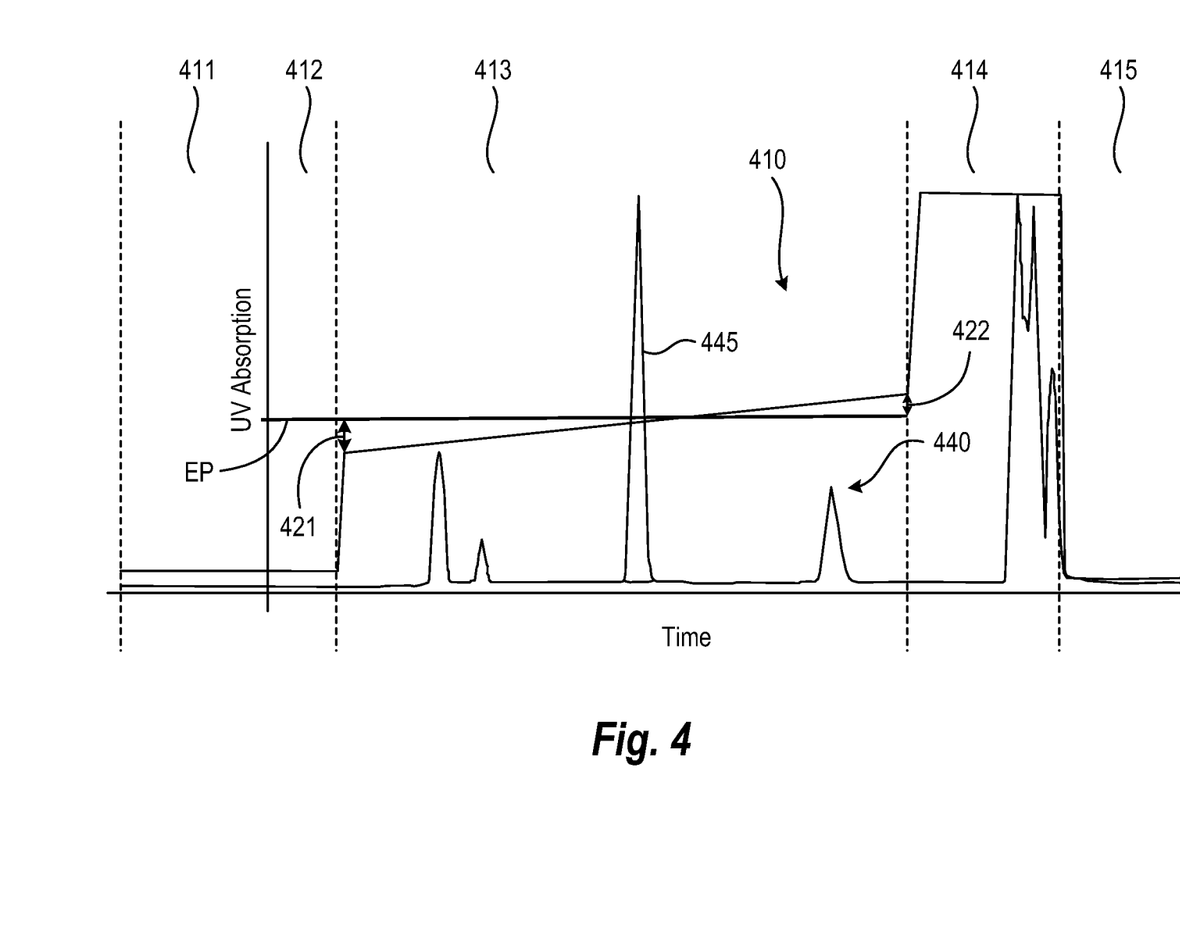
FIG. 4 is a diagram showing chromatographic results of a preparative run using a focusing gradient, according to a representative embodiment.

FIG. 2 is a flow diagram depicting a method of isolating a compound in a sample by chromatography, according to a representative embodiment. FIG. 3 is a diagram showing chromatographic results of an analytical run using an analytical gradient, according to a representative embodiment. FIG. 4 is a diagram showing chromatographic results of a preparative run using a focusing gradient, according to a representative embodiment.

Referring to FIGS. 1 and 2, an analytical gradient for analytical system 120 is determined in block S211. The analytical gradient (which may also be referred to as a generic or ballistic gradient) generally determines the concentration of organic solvent in the solvent mixture over time during the analytical run, where the solvent mixture flows at a constant analytical pump flow of the analytical system 120.

As shown in FIG. 3, for example, illustrative analytical gradient 310 consists of multiple segments, including isocratic hold segment 312, slope segment 313, flushing (or purging) segment 314, and re-equilibration segment 315. The analytical gradient 310 starts with the isocratic hold segment 312, which provides an initial hold time, during which the concentration of the organic solvent in the solvent mixture is maintained at a relatively low percentage. In the depicted example, the initial hold time provided by the isocratic hold segment is about one minute, and the concentration of the organic solvent concentration is held at about 2 percent. The isocratic hold segment 312 is followed by the slope segment 313, during which the concentration of the organic solvent is linearly increased to a level where the solvent mixture consists almost entirely of the organic solvent. This effectively ensures that the compounds in the sample elute off the analytical column 125. In the depicted example, the concentration of the organic solvent linearly increases from about 2 percent to about 98 percent over a time period (slope duration) of about 9.6 minutes.

The slope segment 313 is followed by the flushing segment 314, during which the concentration of the organic solvent is maintained at the high level attained at the end of the slope segment 313 (e.g., about 98 percent) over a time period (flushing duration) sufficient to assure that all compounds are flushed from the analytical column 125. The flushing segment 314 is followed by the re-equilibration segment 315, during which the concentration of the organic solvent drops to the initial relatively low level (e.g., about 2 percent) and is maintained long enough to stabilize the analytical system 120 for the next analytical run. The re-equilibration segment 315 effectively serves the same purpose as the pre-run segment 411 of the preparative focusing gradient 410 discussed below with reference to FIG. 4. In the depicted example, the pump flow of the solution mixture in the analytical run is set to about 1.5 ml/min. Calculation of the analytical gradient 310 for purposes of eluting compounds in a sample would be apparent to one of ordinary skill in the art.

Referring again to FIG. 2, an analytical run is performed in block S212 using the analytical gradient 310 determined in block S211. In block S213, a target compound in the sample is identified using the chromatographic results of the analytical run. More particularly, the chromatographic results indicate elution of the various sample compounds by a series of peaks. For purposes of illustration, the target compound identified (and thus selected for isolation) is indicated by peak 345 of the chromatographic results 340 in FIG. 3, e.g., since it is the largest peak and indicates elution in the middle portion of the slope segment 313. Of course, another peak from the chromatographic results may be selected as corresponding to the target compound, without departing from the scope of the present teachings. In various embodiments, the target compound may be identified manually by a user, for example, by clicking on the peak 345 using a mouse, or automatically using a mass spectrometer (not shown), for example, by preprogramming parameters of the desired target compound which the mass spectrometer then identifies in the chromatographic results.

In block S214, an analytical retention time of the target compound is also determined using the chromatographic results of the analytical run. The analytical retention time is the time at which the target compound elutes off the analytical column 125 (indicated by the time of the apex of the peak 345 of the target compound in the chromatographic results). This time is affected by the slope of the analytical gradient in the slope segment 313.

An elution point of the target compound is determined in block S215 using the analytical gradient 310 determined in block S211, the analytical retention time determined in block S214, and various characteristics of the analytical system 120, as discussed below. The characteristics of the analytical system 120 for determining the elution point of the target compound may include, for example, a dwell volume of the analytical system 120, a column void volume of an analytical column 125, and an analytical pump flow of the solvent mixture through the analytical system 120. In an embodiment, the elution point (EP) of the target compound may be calculated according to Equation (1), in which all times and values correspond to the analytical system 120 or the analytical gradient 310 used for performing the analytical run:

$$EP = \left(t_R - t_I - \frac{(V_D + V_C)}{F_A}\right) * \frac{(c_E - c_S)}{t_G} + c_S \quad (1)$$

In Equation (1), $t_R$ is the analytical retention time determined in block S214, $t_I$ is the initial hold time of the isocratic hold segment 312, $V_D$ is the dwell volume of the analytical system 120, $V_C$ is the column void volume of the analytical column 125, $F_A$ is the pump flow of the solvent solution in the analytical system 120, $c_E$ is the final organic solvent concentration of the analytical gradient 310 at the end of the slope segment 313, $C_S$ is the starting organic solvent concentration of the analytical gradient 310 at the beginning of the slope segment 313, and $t_G$ is the duration of the slope segment 313. The elution point may therefore be seen as the concentration of the organic solvent in the solvent solution at the end of the analytical column 125 at the retention time of the target compound.

Once determined in the analytical system 120, the same analytical elution point of the target compound may be applied to the preparative system 130 for isolating the target compound. More particularly, a focusing gradient of the preparative system 130 is determined automatically in block S216, and a preparative run using the focusing gradient to separate the target compound from the sample is performed in block S217.

FIG. 4, for example, shows an illustrative focusing gradient 410, which is up-scaled from the analytical gradient 310 due to the larger size of the preparative system 130 and the sample as compared to the analytical system 120. The focusing gradient 410 consists of multiple segments, including pre-run segment 411, isocratic hold segment 412, slope segment 413 and flushing (or purging) segment 414. FIG. 4 also depicts re-equilibration segment 415, which effectively corresponds to the pre-run segment of the next application of the focusing gradient 410. Therefore, automatically determining the focusing gradient 410 in block S215 may include automatically determining the pre-run segment 411, the isocratic hold segment 412, the slope segment 413 and/or the flushing segment 414, discussed below.

The focusing gradient 410 starts with the pre-run segment 411, which may also be referred to as the column equilibration segment. The pre-run segment 411 consists of a pre-run time ($t_{Pre-Run}$), which may be calculated according to Equation (2):

$$t_{Pre-Run} = 3 \cdot \frac{(V_{D,P} + V_{C,P})}{F_P} \quad (2)$$

In Equation (2), $V_{D,P}$ is the dwell volume of the preparative system 130, $V_{C,P}$ is the column void volume of the preparative column 135, and $F_P$ is the pump flow of the solvent solution in the preparative system 130. The concentration of the organic solvent in the solvent mixture is maintained at a relatively low percentage (e.g., about 2 percent) during the pre-run segment 411 of the focusing gradient 410.

The pre-run segment 411 is followed by the isocratic hold segment 412, which is essentially an up-scaled version of the isocratic hold segment 312 of the analytical gradient 310, thus accounting for the larger size of the preparative system 130. Examples of up-scaling an hold segment are provided by Guillarme et al. The isocratic hold segment 412 consists of an initial hold time ($t_{I,P}$). In the depicted example, the concentration of the organic solvent concentration is held at about 2 percent during the isocratic hold segment 412. The initial hold time ($t_{I,P}$) may be calculated according to Equation (3):

$$t_{I,P} = \frac{(V_{D,A} + t_{I,A} \cdot F_A)}{V_{C,A}} \cdot \frac{V_{C,P}}{F_P} - \frac{V_{D,P}}{F_P} \quad (3)$$

In Equation (3), $t_{I,A}$ is the initial hold time of the isocratic hold segment 312 of the analytical gradient 310, $V_{D,A}$ is the dwell volume of the analytical system 120, $V_{C,A}$ is the column void volume of the analytical column 125, and $F_{C,A}$ is the pump flow of the solvent solution in the analytical system 120. The concentration of the organic solvent in the solvent mixture is maintained at a relatively low percentage (e.g., about 2 percent) during the isocratic hold segment 412.

The isocratic hold segment 412 is followed by the slope segment 413, during which the concentration of the organic solvent is linearly increased along an automatically determined slope. More particularly, the slope segment 413 of the focusing gradient 410 includes a slope that determines the concentration of organic solvent in the solvent mixture flowing through the preparative system 130, where the organic solvent concentration linearly increases from a first offset 421 below the elution point (EP) of the target compound (as determined according to Equation (1)) to a second offset 422 above the elution point of the target compound.

In an embodiment, the first offset 421 is about 15 percent below the elution point and the second offset 422 is about 5 percent above the elution point, which effectively may be considered first and second default values, respectively. Thus, generally, the solvent concentration increases from an initial solvent concentration in the isocratic hold segment 412 to the first offset 421 below the elution point substantially at a transition between the isocratic hold segment 412 and the slope segment 413. The initial solvent concentration may be substantially the same as the solvent concentration in the isocratic hold segment 312 of the analytical gradient 310. The solvent concentration then increases from the first offset 421 below the elution point to the second offset 422 above the elution point in the slope segment 413.

Generally, according to the present embodiment, the first offset of about 15 percent below the elution point and the second offset of about 5 percent above the elution point have been determined empirically and do not vary. That is, without user interaction, the proposed focusing gradient will have 15 percent as the first offset 421 and 5 percent as the second offset 422. These values are designed to let sample compounds with an S-parameter close to 15, as discussed below with reference to Equation (4), elute substantially in the middle of the slope segment 413 of the focusing gradient 410. Only the lengths of one or more different segments of the focusing gradient 410 are changed, e.g., due to preparative system 130 and/or preparative run characteristics, such as the sizes of the inner diameters and lengths of the preparative column 135, the relative positioning of the elution point of the target compound, and the like. However, the first and second offsets 421 and 422 may be changed if the user decides to manually increase or decrease the duration of the isocratic hold segment 412 and/or the slope segment 413. For example, the first and second offsets 421 and 422 of the slope may be adjusted based on an amount a time of the slope duration of the slope segment 413 differs from a predetermined default time, so that the target compound elutes in the same portion of the slope segment 413. The initial values of the first offset 421 (e.g., about 15 percent below the elution point) and the second offset 422 (e.g., about 5 percent above the elution point) correspond to a predetermined default time of the slope segment 413 (e.g., about 6 minutes).

When scaling up from an analytical column 125 with small particle sizes (e.g., about 1.8 μm) in an analytical run to a preparative column 135 with larger particle sizes (e.g., about 5 μm) in a preparative run, the resulting duration of the isocratic hold segment 412 and the slope segment 413 of the focusing gradient 410 may become undesirably large. In such cases, the respective durations of the isocratic hold segment 412 and the slope segment 413 may be decreased by a given factor. For this purpose, the first and second offsets 421 and 422 around the point of elution of the target compound are also adjusted in order to maintain the (time) percentage of the slope segment 413 after which the target compound is eluting. For example, if the target compound was eluting after about 40 percent of the duration of the slope segment 413 in the default focusing gradient, the target compound will likewise elute after about 40 percent of the duration of the slope segment 413 in the adjusted focusing gradient, which includes the decreases in the durations of the isocratic hold segment 412 and the slope segment 413, and the adjustments to the first and second offsets 421 and 422.

The adjustments to the first and second offsets 421 and 422 are based on numerical simulations of movement (within the preparative column 135) of a given compound with an S-parameter equal to 15 and a $k_0$ parameter calculated from the analytical run, where the S- and $k_0$ parameters are parameters of a model that describes retention factors (k) in gradient elution. For example, the retention factor k may be calculated according to Equation (4):

$$k = k_0 \cdot e^{-S \cdot \phi} \qquad (4)$$

In Equation (4), $k_0$ is the retention factor in pure water, S is a model parameter and $\phi$ is the percentage of organic solvent in the solvent mixture. In general, the S- and $k_0$ parameters for a given compound may be calculated from two runs with different gradients differing in slope (e.g., a first gradient from 2 percent to 98 percent in 9 minutes and a second gradient from 2 percent to 98 percent in 3 minutes). Empirically, it was determined that with an S-parameter equal to 15, all tested target compounds still elute within the slope segment 413 of the focusing gradient 410 after the adjustments of the first and second offsets 421 and 422. Determination of the retention factor k is described, for example, by Schoenmakers et al., *Gradient Selection in Reversed-Phase Liquid Chromatography*, Journal of Chromatography 149, pp. 519-537 (1978) (hereinafter "Schoenmakers et al."), the entire subject matter of which is hereby incorporated by reference.

In the present embodiment, there is only one run (the analytical run), as opposed to two. However, after analyzing a number (e.g., 50) of different typical compounds and measuring corresponding S- and $k_0$ parameters, it was determined that all of the compounds could be treated as having S equal to 15 without introducing too large of an error when only adjusting the first and second offsets 421 and 422 around the elution point. It is therefore assumed that the S-parameter is equal to 15 for all compounds, in which case the $k_0$ parameter may be calculated for a given compound from only one analytical run. Having the S-parameter and $k_0$ parameter, one is able to calculate the retention factor of the compound at every possible time or location inside the column (e.g., the preparative column 135). As discussed by Schoenmakers et al., for example, moving velocity (v) of a compound within the column may be calculated according to Equation (5):

$$v = u/(1+k) \qquad (5)$$

In Equation (5), u is the velocity of the mobile phase, and k is the retention factor (mentioned above). Using the moving velocity v, a numerical simulation may be implemented describing movement of the compound within the column. For example, the numerical simulation may simply involve making several small time steps, and calculate the new velocity and the new location of the compound within the column. This enables prediction of the retention time of a particular compound for a given focusing gradient. In this way, the first and second offsets 421 and 422 for the adjusted (e.g., decreased) isocratic hold segment 412 and slope segment 413 may be optimized, such that the target compound elutes at the same (time) percentage of the slope segment 413 as it would for the default focusing gradient (e.g., without the decreased isocratic hold segment 412 and slope segment 413).

The slope segment 413 is followed by the flushing segment 414. The flushing segment 414 consists of a flush time ($t_{Flush}$), during which any remaining compound or residue from the sample is flushed from the preparative column 135. In the depicted example, the concentration of the organic solvent in the solvent mixture is maintained at a relatively high percentage (e.g., about 98 percent) during the flushing segment 414. The flush time ($t_{Flush}$) may be calculated according to Equation (6):

$$t_{Flush} = \frac{2 \cdot V_{D,P} + 3 \cdot V_{C,P}}{F_P} \quad (6)$$

Thus, generally, the solvent concentration increases from the second offset 422 above the elution point at the end of the slope segment 413 to an ending solvent concentration in the flushing segment 414 substantially at a transition between the slope segment 413 and the flushing segment 414. The ending solvent concentration may be substantially the same the solvent concentration in the flushing segment 314 of the analytical gradient 310.

In an embodiment, the flushing segment 414 may be followed by re-equilibration segment 415, during which the concentration of the organic solvent drops to the initial relatively low level (e.g., about 2 percent) and is maintained long enough to stabilize the preparative system 130 for the next preparative run. As mentioned above, the re-equilibration segment 415 may effectively serve as the pre-run segment 411 of the next focusing gradient 410.

It is generally known that preparative pump flow can be calculated from the analytical and preparative column geometries and the dwell volumes of the analytical and preparative systems. See, e.g., Guillarme et al. In case the user does not use this proposed preparative pump flow, the initial holding time of the isocratic hold segment 412, as well as the slope duration of the slope segment 413, may be multiplied by the ratio of the proposed preparative pump flow and the actual preparative pump flow to adjust accordingly.

When the user has applied an analytical gradient that has a slope that is different from the slope of the generic analytical gradient (e.g., analytical gradient 310), a second correction may be applied. Then, the slope duration of the slope segment of the focusing gradient applied in the preparative run is changed such that the ratio of the slope of the resulting focusing gradient and the slope of the generic focusing gradient (e.g., from the elution point minus 15 percent to the elution point plus 5 percent across the slope segment) is the same as the ratio of the slope of the analytical gradient and the slope of the generic analytical gradient. Again, these corrections are applied in order to allow sample compounds with an S-parameter close to 15 to elute in substantially the middle of the slope phase. As a practical matter, though, the slope of the slope segment 413 of the focusing gradient 410 is flatter than a slope of the slope segment 313 of the analytical gradient 310. This is because the concentration of organic solvent in the solvent mixture is purposefully focused around the elution point of the target compound (known as a result of the analytical run).

Figure 5:
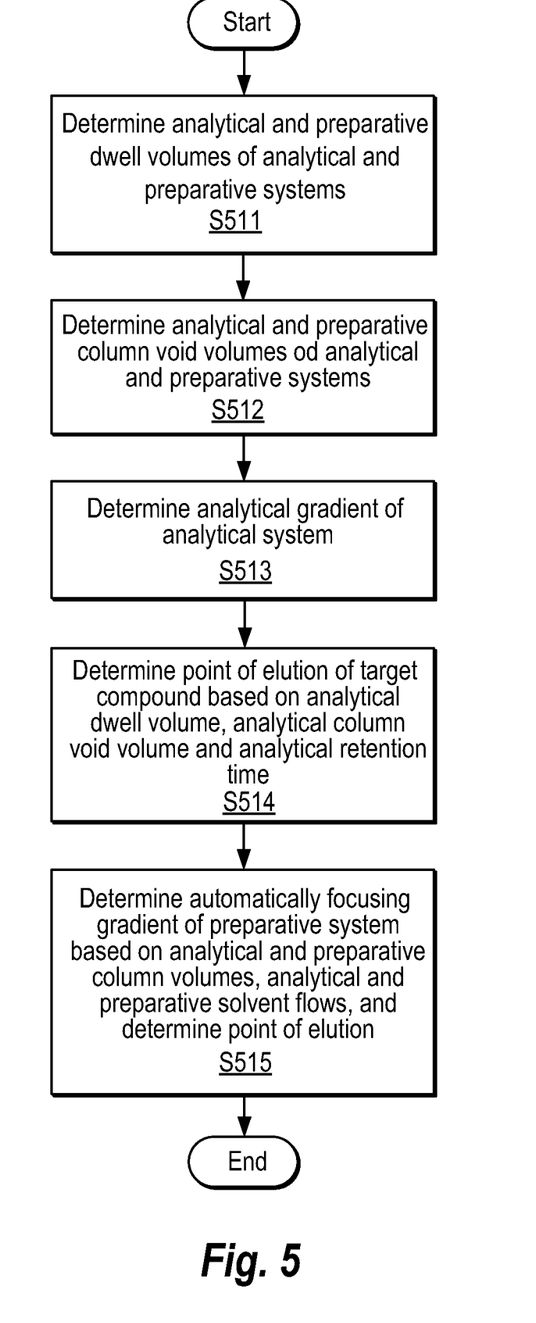
FIG. 5 is a flow diagram depicting a method of isolating a compound in a sample by chromatography, according to a representative embodiment.

FIG. 5 is a flow diagram depicting a method of isolating a compound in a sample by chromatography, according to a representative embodiment. The method of FIG. 5 follows a different approach than the method of FIG. 2, arriving at substantially the same result.

Referring to FIGS. 1 and 5, an analytical dwell volume of the analytical system 120, and a preparative dwell volume of the preparative system 130 are determined in block S511. Likewise, an analytical column void volume of the analytical column 125 in the analytical system 120, and a preparative column void volume of the preparative column 135 in the preparative system 130 are determined in block S512.

In block S513, an analytical gradient (e.g., analytical gradient 310) of the analytical system is determined, and an analytical run is performed using the analytical gradient. Then, in block S514, a point of elution of a target compound, selected from among multiple compounds in a sample, is determined based on at least the analytical dwell volume determined in block S511 and the analytical column void volume determined in block S512, as well as an analytical retention time of the target compound obtained using chromatographic results of the analytical run using a solvent mixture having a concentration of organic solvent that linearly increases in accordance with a slope in a slope segment of the analytical gradient. The solvent mixture may be a varying mixture of acetonitrile and water, for example.

A focusing gradient (e.g., focusing gradient 410) of the preparative system 130 is determined automatically in block S515 based on at least the analytical and preparative dwell volumes determined in block S511, the analytical and preparative column void volumes determined in block S512, analytical and preparative pump flows of the solvent mixture, and the point of elution of the target compound determined for the analytical system 120 in block S514. Automatically determining the focusing gradient includes determining a slope, which determines the concentration of the organic solvent in the solvent mixture. The slope shows the concentration of the organic solvent linearly increasing from a first offset (e.g., first offset 421) below the point of elution of the target compound at a beginning of a slope segment of the focusing gradient to a second offset (e.g., second offset 422) above the point of elution of the target compound at an end of the slope segment of the focusing gradient.

As discussed above, determining the slope of the slope segment in the preparative gradient may include adjusting the first offset from a first default value at the beginning of the slope, and adjusting the second offset from a second default value at the end of the slope, so that the target compound elutes in the same portion of the slope segment as it elutes in the analytical gradient. The first and second default values may correspond to a predetermined default time period of a slope segment (slope duration) and a predetermined default length of a preparative column used to determine a generic preparative gradient. For example, the predetermined default time may be about 6 minutes and the predetermined length of the generic preparative column may be about 150 mm, as discussed above. Generally, the predetermined default time period of the slope segment is approximately 2 minutes for each 50 mm length of the preparative column.

In an illustrative configuration using the above values, the first default value below the point of elution of the target compound may be approximately 15 percent, and the second default value above the point of elution of the target compound may approximately 5 percent. The first and second offsets 421 and 422 of the slope in the slope segment of the preparative gradient may therefore be adjusted based on the amount the time period of the slope segment 413 (i.e., the slope duration) differs from the predetermined default time period. If the length of the preparative column is different from a default length, then the default time period of the slope segment changes.

Automatically determining the focusing gradient in block S515 may further include determining a preparative column equilibration segment or pre-run segment (pre-run segment 411), determining an isocratic hold segment (e.g., isocratic hold segment 412) between the pre-run segment and the slope segment, and determining a flushing segment (e.g., flushing segment 414) after the slope segment. The various segments of the focusing gradient may be determined in accordance with Equations (2) to (6), above. In various embodiments, the focusing gradient includes the slope segment, and less than all of the pre-run segment, the isocratic hold segment and the flushing segment, without departing from the scope of the present teachings.

As discussed above, the pre-run segment may be determined automatically based on the preparative dwell volume, the preparative column void volume, and the preparative pump flow of the solvent mixture in the preparative system during a preparative run. Also, the isocratic hold segment may be determined automatically based on an initial hold of the analytical gradient, the analytical dwell volume, the analytical column void volume, analytical pump flow, preparative pump flow, preparative dwell volume, and preparative column void volume. Also, the flushing segment may be determined automatically based on the preparative dwell volume, the preparative column void volume, and the preparative pump flow.

In summary, a focusing gradient may be automatically determined for any target compound using the analytical gradient, the analytical retention time, the analytical and preparative column dimensions (column void volumes), the analytical and preparative dwell volumes, and the analytical and preparative pump flows.

Embodiments described herein, including the various operations depicted in FIGS. 2 and 5, may be stored as code on a non-transitory computer readable medium and/or executed by one or more processing devices, such as processing device 170 in FIG. 1. As discussed above, the processing device may be implemented by one or more computer processors, ASICs, FPGAs, or combinations thereof, using software, firmware, hard-wired logic circuits, or combinations thereof. When using a computer processor, a memory may be included for storing executable software/firmware and/or executable code that allows it to perform the various functions. The memory may include any number, type and combination of random access memory (RAM) and read-only memory (ROM), for example, such as a disk drive, an electrically programmable read-only memory (EPROM), an electrically erasable and programmable read only memory (EEPROM), a CD, a DVD, a universal serial bus (USB) drive, and the like, which are non-transitory (e.g., as compared to transitory propagating signals). The memory may store various types of information, such as computer programs and software algorithms executable by the computer processor, to perform steps for isolating a compound in a sample using chromatography and/or controlling the chromatography process. Further, users may interface with the processing device and/or the memory through an I/O interface using various input device(s), such as a keyboard, a track ball, a mouse, a touch pad, touch-sensitive display, and the like, for example. Also, various information, such the chromatography results and applied analytical and preparatory gradients, may be displayed on a display through a display interface, which may include any type of graphical user interface (GUI). The type, number and arrangement of interfaces may vary without departing from the scope of the present teachings.

In accordance with illustrative embodiments, all or part of methods described for isolating and/or analyzing a compound in a sample using chromatography may be executable by a processing device and/or stored as code on a computer readable medium. One of ordinary skill in the art appreciates that many variations that are in accordance with the present teachings are possible and remain within the scope of the appended claims. These and other variations would become clear to one of ordinary skill in the art after inspection of the specification, drawings and claims herein. The invention therefore is not to be restricted except within the spirit and scope of the appended claims.

What is claimed is:

1. A method of isolating a compound in a sample, comprising a plurality of compounds, by chromatography, the method comprising:
   determining an analytical gradient of an analytical system;
   performing an analytical run using the analytical gradient;
   identifying a target compound in the sample using chromatographic results of the analytical run;
   determining an analytical retention time of the target compound using the chromatographic results of the analytical run;
   determining an elution point of the target compound using the analytical retention time, the analytical gradient and characteristics of the analytical system;
   determining automatically a focusing gradient of a preparative system, up-scaled from the analytical gradient, the focusing gradient including a slope segment; and
   performing a preparative run using the focusing gradient to separate the target compound from the sample,
   wherein the slope segment of the focusing gradient includes a slope determining a concentration of solvent in a solvent mixture, the concentration linearly increasing from a first offset below the elution point of the target compound to a second offset above the elution point of the target compound.

2. The method of claim 1, wherein the focusing gradient further includes an equilibration segment, an isocratic hold segment between the equilibration segment and the slope segment, and a flushing segment after the slope segment.

3. The method of claim 2, wherein the solvent concentration in the solvent mixture increases from an initial solvent concentration in the isocratic hold segment to the first offset below the elution point at a transition between the isocratic hold segment and the slope segment.

4. The method of claim 3, wherein the initial solvent concentration is substantially the same as the solvent concentration in an isocratic hold segment of the analytical gradient.

5. The method of claim 3, wherein the solvent concentration in the solvent mixture increases from the second offset above the elution point to an ending solvent concentration in the flushing segment at a transition between the slope segment and the flushing segment.

6. The method of claim 5, wherein the ending solvent concentration is substantially the same as a solvent concentration in a flushing segment of the analytical gradient.

7. The method of claim 1, wherein the first offset is approximately 15 percent below the elution point of the target compound, and the second offset is approximately 5 percent above the elution point of the target compound.

8. The method of claim 1, wherein identifying the target compound in the sample comprises manually selecting the target compound.

9. The method of claim 1, wherein identifying the target compound in the sample comprises automatically selecting the target compound using a mass spectrometer.

10. The method of claim 1, wherein the characteristics of the analytical system for determining the elution point of the target compound include a dwell volume of the analytical system, a column void volume of an analytical column in the analytical system, and an analytical pump flow of the solvent mixture through the analytical system.

11. The method of claim 1, wherein
determining the elution point is based on at least an analytical dwell volume of the analytical system, an analytical column void volume of an analytical column of the analytical system, and an analytical retention time of the target compound obtained using the chromatographic results; and
determining automatically the focusing gradient is based on at least the analytical dwell volume, a preparative dwell volume of the preparative system, the analytical column void volume, a preparative column void volume of a preparative column of the preparative system, analytical and preparative pump flows of the solvent mixture, and the determined elution point.

12. The method of claim 1, wherein the first and second offsets of the slope are adjusted based on an amount a time of the slope segment differs from a predetermined default time, so that the target compound elutes in the same portion of the slope segment, and
wherein initial values of the first and second offsets correspond to the predetermined default time of the slope segment.

13. The method of claim 12, wherein the predetermined default time of the slope segment is approximately 2 minutes for each 50 mm length of the preparative column.

14. The method of claim 1, wherein the slope of the slope segment of the focusing gradient is flatter than a slope of a slope segment of the analytical gradient.

15. The method of claim 1, wherein determining automatically the focusing gradient further includes determining a preparative column equilibration segment, determining an isocratic hold segment between the preparative column equilibration segment and the slope segment, and determining a flushing segment after the slope segment.

16. The method of claim 15, wherein the preparative column equilibration segment is determined automatically based on a preparative dwell volume of the preparative system, a preparative column void volume of a preparative column of the preparative system, and a preparative pump flow of the solvent mixture through the preparative system during a preparative run.

17. The method of claim 15, wherein the isocratic hold segment is determined automatically based on an initial hold of the analytical gradient, an analytical dwell volume of the analytical system, an analytical column void volume of an analytical column of the analytical system, an analytical pump flow of the solvent mixture through the analytical system, a preparative pump flow of the solvent mixture through the preparative system, a preparative dwell volume of the preparative system, and a preparative column void volume of a preparative column of the preparative system.

18. The method of claim 15, wherein the flushing segment is determined automatically based on a preparative dwell volume of the preparative system, a preparative column void volume of a preparative column of the preparative system, and a preparative pump flow of the solvent mixture through the preparative system.

19. A chromatographic system, comprising:
an analytical system configured to perform an analytical chromatographic run;
a preparative system configured to perform a preparative chromatographic run; and
a processing device configured to control the analytical system and the preparative system to perform the method of claim 1.

* * * * *